(12) United States Patent
Trunin et al.

(10) Patent No.: US 8,546,611 B2
(45) Date of Patent: Oct. 1, 2013

(54) METHOD FOR PREPARING SUCCINIC ACID

(76) Inventors: Roman Anatolievich Trunin, Moscow (RU); Mikhail Lvovich Uchitel, Mytishi (RU); Evgenij Iljich Maevskij, Pushino (RU); Vladimir Izrailevich Heifets, Tula (RU); Svetlana Yakovlevna Chernitzkaya, legal representative, St. Petersburg (RU); Donna Kasseinova, Palos Verdes Estates, CA (US); Larisa Petrovna Pivonenkova, Tula (RU); Tatiana Borisovna Lubimova, Tula (RU)

( * ) Notice: Subject to any disclaimer, the term of this patent is extended or adjusted under 35 U.S.C. 154(b) by 458 days.

(21) Appl. No.: 13/061,147

(22) PCT Filed: Aug. 24, 2009

(86) PCT No.: PCT/RU2009/000427
§ 371 (c)(1),
(2), (4) Date: Feb. 27, 2011

(87) PCT Pub. No.: WO2010/041977
PCT Pub. Date: Apr. 15, 2010

(65) Prior Publication Data
US 2011/0213183 A1   Sep. 1, 2011

(30) Foreign Application Priority Data
Aug. 28, 2008 (RU) ................................ 2008134835

(51) Int. Cl.
*C07C 55/10* (2006.01)
*C07C 51/36* (2006.01)

(52) U.S. Cl.
USPC ........................................................ 562/592

(58) Field of Classification Search
None
See application file for complete search history.

(56) References Cited

FOREIGN PATENT DOCUMENTS
RU          2237056       *   9/2004

* cited by examiner

*Primary Examiner* — Yevegeny Valenrod
(74) *Attorney, Agent, or Firm* — Bardmesser Law Group

(57) ABSTRACT

A method for preparing succinic acid, including producing a modified palladium-containing catalyst by using an acid and liquid-phase hydrogenation of unsaturated acid compounds on the modified catalyst at an increased temperature and pressure; separating the catalyst from the succinic acid; wherein the modification of the catalyst is performed on a substrate having the palladium-containing catalyst delivered thereon, the delivery being performed in an oxygen-free atmosphere; the delivery being performed in an aqueous medium of succinic, maleic or fumaric acids and/or their mixtures at a $Pd^{2+}$/acid ratio of 1:1-1:100; hydrogenating the liquid-phase unsaturated acid compounds selected from maleic, fumaric acids or their anhydrides or their mixtures; and crystallizing the succinic acid from an aqueous solution containing 0.001-0.01 wt. % succinic acid seed.

6 Claims, No Drawings

METHOD FOR PREPARING SUCCINIC ACID

CROSS-REFERENCE TO RELATED APPLICATION

This application is a National Phase of PCT/RU2009/000427, filed on Aug. 24, 2009, which claims priority to RU 2008134835, filed on Aug. 28, 2008, which are incorporated by reference herein in their entirety.

FIELD OF THE INVENTION

The present invention relates to a method for synthesis of biologically active succinic acid (SA), which is widely used in medicine, nutrition and cosmetic industries.

BACKGROUND OF THE INVENTION

SA is one of the indispensable metabolites of energy cycle in all living organisms, both plant and animal. In animals, it also provides—in cooperation with orphan receptors—a number of signal functions.

The medicinal features of SA have been known since the 15th century and were first described in the pharmacopeia of an Armenian physician Amasiatsi in 1493 (see "Garbage for Ignoramus", medieval encyclopedia, http:**libbox.info/book_reading_91900.html).

SA possesses a large number of features: it "catalytically" contributes to the activation of energy exchange and has a cardiotonic, radioprotective and mild diuretic effect.

However, experiments show that SA samples of "natural" (i.e., obtained from amber) and synthesized by various methods are not identical in their biological activity. Synthetic samples mainly have evident diuretic and, to some extent, energizing features. We have conducted a number of tests, which allow one a reliable determination of SA biological activity; among them are those that provide technological control over the production released. We have examined more than 150 samples obtained with a variety of techniques. Since there are no physical-chemical methods, which would allow one to reveal differences between samples, we have conducted and applied biological tests, that reliably measure biological activity.

Several methods of SA synthesis are known. They utilize different kinds of raw materials: first of all, maleic anhydride, maleic acid, butadiene rubbers, furfural, etc. As a rule, the authors of the patents below do not declare the level of SA biological activity.

A method of SA synthesis that "reveals various kinds of biological activity" (RU Patent No. 2236398) is based on the oxidation of furfural with hydrogen peroxide, with the further addition of an alkaline reagent at variable pH (from <4 to 7), followed by neutralization, evaporation and re-crystallization from acetone and water to purify the product from traces of maleic, fumaric and oxalic acids (Patent RU 2098804). With all the obvious technological complexity of the synthesis (a lot of stages and use of a flammable organic solvent, requiring special use conditions) and the necessity of an additional stage of re-crystallization, it is almost impossible to achieve the 90% product yield declared by authors. The biological activity of SA obtained by this method is limited: according to the tests conducted, this acid is mainly a diuretic. In addition, the method does not produce the substance that would meet food safety requirements: the product contains a lot of harmful impurities.

There are numerous methods of SA synthesis through the liquid-phase catalytic reduction of maleic anhydride (maleic acid) at increased temperature and pressure.

The catalysts used in the known methods of SA synthesis are group VIII metals (nickel, ruthenium, palladium, rhodium or platinum), being either in the form of skeletal contact or applied on various supports (activated carbon, alumina, kieselguhr, asbestos etc.)

A common shortcoming of all these methods is the use of contacts with a high content of precious metals and the low product yield per unit weight of active component.

Data on the biological activity of SA obtained with the above-mentioned methods are not available in the patents noted above.

In RU Patent No. 2129540, hydrogenation of maleic anhydride or maleic acid in water is performed in the presence of a palladium-containing supported catalyst, with a palladium-nickel or palladium-iron catalyzing contact. This method allows one to achieve a high yield of SA (up to 99.7%), along with high productivity and good quality (melting temperature, 186.8-187.0° C.; main substance content, up to 99.8%; no impurities, i.e., maleic or fumaric acid).

According to our tests, a shortcoming of this method is that the biological activity of the highly purified SA synthesized by hydrogenation differs from that of natural SA obtained by pyrolysis of amber crumb.

A method of synthesis of highly purified, biologically active SA by hydrogenation of maleic anhydride (maleic or fumaric acids) in the aqueous medium on a heterogeneous catalyst is known, whose active phase is a complex compound of palladium and iron with succinic, maleic or fumaric acids or their alkalic salts (RU Patent No. 2237056). The catalytic complexes are applied on a support at the moment of their formation. Succinic acid obtained by this method possesses biological properties similar to those of natural SA.

A shortcoming of this method is the necessity of a separate preliminary multi-stage procedure for synthesis of the catalyst, which includes:

preparation of 3-4 initial solutions;
slurrying of supporting material;
consecutive dosing of initial solutions under pH-monitoring;
incubation at certain temperatures after dosing of each initial solution;
filtration of catalyst suspension;
washing of catalyst on a filter;
drying of catalyst to a certain residual moisture.

As a result of complexity of this procedure, one would encounter problems with the conversion of a laboratory setup to a production unit and with instability of biological activity of SA obtained on apparatus of different type (see the results of tests according to the technique described in example 13 RU Patent No. 2237056). Less than 60% of the laboratory-synthesized SA samples were biologically active. Among the industrially produced samples, which were synthesized according to the procedure described above, only 12% of batches had appropriate values of biological activity.

The objective of the proposed method is to simplify the method of SA synthesis, so that the product would be of high purity and, at the same time, possess a stable high biological and adaptogenic activity.

This objective is achieved by (1) elimination of the separate stage of catalyst synthesis with its preliminary separation, (2) improvement (simplification) of the procedure of obtaining the hydrogenation catalyst, and (3) application of a seed on the stage of crystallization, which should be SA with high biological activity.

In one aspect, a method for preparing the succinic acid with a stably high biological and adaptogenic activity, includes the stages of producing a modified palladium-containing catalyst by using an acid and liquid-phase hydrogenation of unsaturated acid compounds on the said modified catalyst at an increased temperature and pressure, with further separation of the catalyst and the succinic acid, where the modification is performed over a prefabricated palladium-containing catalyst covering a carrier, in an oxygen-free atmosphere, in an aqueous medium of succinic, maleic or fumaric acids and/or their mixtures at the $Pd^{2+}$/acid ratio of 1:1-1:100; thereupon, the process of liquid-phase hydrogenation of unsaturated acid compounds selected from maleic, fumaric acids or their anhydrides or their mixtures, is performed, and the product resulted from the hydrogenation process is obtained by crystallization from the aqueous solution containing 0.001-0.01 wt. % seed represented by the succinic acid with high biological activity.

The conducted experiments showed that a catalyst with desirable features (active and selective towards hydrogenation of maleic anhydride and maleic/fumaric acids into highly bioactive SA) can be obtained by preliminary (right before hydrogenation) modification of any palladium-containing supported catalyst with maleic, fumaric or succinic acids.

The modification of palladium catalysts with the aforementioned acids is conducted in aqueous solutions of these acids in an oxygen-free atmosphere. The concentration of the catalyst suspension in the aqueous solution and the palladium/acid ratio are maintained within the range of 0.1-1.5 wt. % and 1:1-1:100 respectively. It is possible to use a higher acid/palladium ratio; however, this will result not only in the absence of any extra positive effect but also in the danger of palladium being transferred from the catalyst surface into the solution, this decreasing the catalyst activity. The concentration of supported palladium can be altered within 0.1-1.0 wt. %, with the concentration of acids-modifiers varying within 0.01-0.7%—depending on the concentration of supported palladium and the chosen palladium/acid ratio. The duration of modification was 0.5-2 hours.

The process of modification can be carried out right in the hydrogenation reactor, under an oxygen-free atmosphere, with constant stirring, and within a wide range of temperatures: 5-70° C. (preferably, 15-40° C.).

After the process of modification is finished, the reactor is loaded with maleic anhydride (maleic or fumaric acids), and the system is purged with hydrogen, this followed by setting the necessary temperature condition and hydrogen pressure. The process goes at temperature 100-120° C. and pressure not more than 25 atm. A higher pressure does not give an additional positive effect. After the hydrogen consumption is finished, and the reaction mixture having been incubated for some time, the catalyst is separated by "hot" filtration, followed by feeding the catalyst (aqueous solution of succinic acid with a temperature 80-100° C.) into a heated crystallizing tank, previously supplied with a so-called "seed", an etalon acid of natural origin or equally bioactive. The crystallization is performed in a regime of regulated temperature lowering: first at a rate 3-4°/min (up to 45° C.), then 1-2°/min (to 25° C.), and finally 0.3-0.5°/min (to 5-15° C.). This procedure yields a fine-crystalline precipitate of SA, which is then filtered and dried at a temperature not more than 100° C.

The SA obtained according to this procedure (after separation of source solution and drying) has a high purity (main substance content, not less than 99.0%; no maleic and fumaric acids) and does not differ in biological activity from the acid used as the "seed" of crystallization.

The advantages of the proposed method are obvious: its implementation would substantially simplify the entire technological process of SA synthesis (including the synthesis of catalyst) and also reduce its cost. Tests have shown that the SA produced by this method is characterized by a high biological activity—as high as that of the prototype and even higher in some cases. A peculiar feature of the SA obtained by the method proposed is the stability of its biological activity, whose parameters are independent of the scale of industrial production. The high bioactivity has been confirmed by testing samples according to the technique by example 13. The tests has shown requirements compliance of samples in 92% of cases—independently of the production scale (laboratory or industrial).

The proposed method also allows one to implement the production process with a wide range of modern supported catalysts, which have palladium as their active phase.

Implementation of the technique is illustrated by the examples given below. Examples 1, 2 and 3 show data for conventional analog and the conventional prototype. Examples 4-10 illustrate the invention. We used "natural" SA obtained by pyrolysis of amber crumb as a control. Examples 11-14 present the results of testing samples 1-10 for bioactivity, with the "natural" SA used as a control.

EXAMPLE 1

Prior Art

The synthesis of succinic acid by oxidation of furfural is conducted in a laboratory apparatus (a flask with a backflow condenser put into a boiling water bath). The flask is loaded with 200 cm³ of 30% hydrogen peroxide, 250 cm³ of water and 48 g of furfural. Then, concentrated sodium hydroxide is added under stirring, so as to maintain pH of the medium at a level 2-4 for 45 min Finally, pH is adjusted to 7.

After residual peroxides are decomposed, the reaction mass is supplemented with 100 cm³ of 30% hydrochloric acid and evaporated almost to dryness. The rest is successively re-crystallized from acetone and water, this giving succinic acid with melting point 182.5-183.5° C. (the yield is 74% of theoretically expected).

EXAMPLE 2

Prior Art

Hydrogenation of maleic acid is conducted in a batch-operation apparatus, consisting of a hydrogenation reactor, heated catalyst-separating filter, crystallization tank with a cooling jacket and mixer, filter for separation of succinic acid or its salts, and steam-heated dryer.

The reactor is loaded with 12 liters of water, 4 kg of maleic acid and 32 g of nickel-palladium catalyst (palladium content, 0.2 wt. %; nickel content, 0.2 wt. %). The process of hydrogenation is conducted in a polythermal regime ($T_{ini}$, 25-30° C.; $T_{fin}$, 95-105° C.) at the constant hydrogen pressure of 10 atm. The hydrogen consumption lasts 100 min. After purging the reactor with nitrogen and separating the catalyst on a heated filter by crystallization and filtration, succinic acid (melting point 186.0-186.5° C.) is isolated, with the total yield (after 3 cycles) amounting to 99.5% of theoretically expected.

EXAMPLE 3

Prototype

Reproduction of Example 2A

Example 2A

Preparation of catalyst with the rated content of palladium 0.1% and iron 0.1% (in reference to the dry mass of supporting material, coal mark OU-B) in an apparatus, which consists of four reservoirs with mixers for preparation of initial solutions, a reactor for synthesis and a filter bag.

1 N solution of sodium hydroxide is prepared in a reservoir of V=5 dm$^3$, by loading 3.25 dm$^3$ of distilled water and 135.5 g of sodium hydroxide (main substance content, 99.0%).

18.4 g of ferric chloride (FeCl$_3$.6H$_2$O) are dissolved under stiffing in 0.9 dm$^3$ of distilled water in a reservoir of V=2 dm$^3$.

The solution of complex palladium salt (chloride-palladium complex) is prepared in a heating-controlled reservoir of V=0.5 dm$^3$ with a mixer and backflow condenser. The reservoir is successively loaded, under continuous stirring, with 2 dm$^3$ of distilled water, 0.5 dm$^3$ of concentrated hydrochloric acid, 2.2 g of sodium chloride and—a little at a time—with 6.78 g of palladium chloride (palladium content, 59 wt. %). The reaction mass is heated to 60-70° C. and stirred until a solution of chloride-palladium complex is formed, which is cooled to 30-40° C. The complex is then hydrolized: the solution is slowly supplemented with ~55 ml of 1N sodium hydroxide and incubated for two hours.

The reactor for synthesis is loaded, under stirring, with 40 dm$^3$ of water, 37.0 g of maleic anhydride or 43.8 g of maleic acid and then with 4 kg (dry weight) of birch coal-clarifier mark OU-B. The heating jacket of the reactor is filled with steam, and the reaction mass is heated to 50±2° C. The heated suspension is supplemented with the solution of sodium hydroxide until pH reaches 9 and then, slowly, with the solution of palladium complex and with ~0.9 dm$^3$ of ferric chloride solution, pH of the suspension being maintained at a level 9-9.5. After all the components has been dosed, the suspension remains for 0.5 hours. Then it is cooled to 30-40° C. and filtered through a filter bag under nitrogen pressure (0.2-0.3 MPa), the filtrate being separated from the catalyst and directed into a collector.

The washed catalyst is dried with nitrogen on a filter to residual moisture ~55% and unloaded as a wet paste (~3.8 kg in recalculation to dry weight).

According to the data of atomic-absorption spectrometry, the catalyst contains, in reference to dry weight, 0.11% palladium and 0.15% iron.

Hydrogenation of maleic anhydride in the presence of the palladium-iron catalyst synthesized is performed in an experimental batch-operation apparatus, which consists of a suspensor and hydrogenating reactor of 100 dm$^3$ each, a heated catalyst-separating Druck-filter, crystallizing tank and product-separating Nutsche-filter.

The process is carried out at a temperature 40-105° C. and under gauge pressure of hydrogen (15 atm). With the catalyst separated by hot filtration and the product crystallized by cooling the hydrogenation catalisate from 90 to 10° C., the yield of succinic acid amounts to 80 and 95.8% of theoretically expected (after the 1st and 2nd cycles of source solution recycling respectively). The quality of succinic acid is high (Tm=187-187.5° C.; assay, 99.6%; no unsaturated acids).

Examples, illustrating the method invented, are presented below. Used as a seed is SA preliminary tested for biological activity; it can be both synthetic or "natural" SA. SA is tested on rats endured an immobilization stress; the parameter tested is lymphocytic composition of blood, which is determined before and after stress in a blood smear taken from the caudal vein. If the eosinophil percentage exceeds 0.5% (optimally 1%), which corresponds to 25 and 50% of the initial level respectively, the acid is suitable for use in the process of crystallization. A detailed description of the testing technique is given in Example 13.

EXAMPLE 4

The modification of catalyst is conducted in a reservoir with a mixer (V=0.3 dm$^3$) loaded with 100 ml of 0.5% maleic acid solution. Air in the apparatus is replaced with argon, and a batch of NPF-1 catalyst (4.6 g) is added. According to the specification, the active phase of this catalyst is palladium in the form of polychloro-hydroxo-complexes promoted with nickel and iron compounds. The contents of palladium, nickel and iron are 0.2, 0.2 and 0.07 wt. % respectively. The suspension of catalyst in water solution of maleic acid is mixed for an hour at a room temperature (~20° C.). Then the suspension of modified catalyst is pushed, under argon pressure, into an autoclave of V=1.0 dm$^3$ previously loaded with 600 ml of 27.7 wt. % water solution of maleic acid. After purging, first with argon and then with hydrogen, the reactor is sealed and its jacket is filled with the heat carrier. Hydrogen pressure is increased to 20 atm, and the mixer is switched on. Hydrogenation (hydrogen consumption) begins right after turning on the mixer. The process is carried out at a temperature ≤90-100° C. After hydrogen consumption is finished and the suspension of catalyst in the solution of succinic acid has stayed for some time at 90-100° C., it is extruded through a heated filter into a crystallizing tank (temperature, ≥80° C.) and supplemented with 0.5 ml of a water solution, containing 0.07 g of succinic acid extracted from the natural amber. The crystallization of succinic acid from the solution is carried out in a regime of controlled cooling:

1st stage (to 45° C.), with the rate 3°/min;
2nd stage (to 25° C.), with the rate 1°/min;
3rd stage (to 10° C.), with the rate 0.3°/min After the sediment is separated from the source solution and dried, the yield of succinic acid amounts to 81.2% of theoretically expected, assay 99.95 wt. %, unsaturated compounds (maleic and fumaric acids) are absent.

After recycling of source solution for three times, the yield of succinic acid increases to 99.5% of theoretically expected.

EXAMPLE 5

20 kg of maleic anhydride are dissolved in 40 liter of water in a suspensor.

The reactor (V=100 dm$^3$) is loaded with 20 liter of water acidified with succinic acid. The concentration of acid in water is 0.012 wt. %. The reactor is purged with nitrogen and then filled with a nitrogen-hydrogen mixture (1:1, volume), followed by loading of POUB-08 catalyst (300 g in recalculation to dry mass), whose active phase, according to the specification, is palladium in reduced form. The catalyst suspension in the diluted solution of succinic acid is preserved under continuous stiffing for 30-40 min, with temperature being gradually increased to 40-50° C.

After modification of catalyst is finished, the reactor is fed a water solution of maleic anhydride (maleic acid), which is pushed into the reactor under nitrogen pressure from the suspensor (suspension reactor). The nitrogen-hydrogen mixture in the reactor is replaced with hydrogen, and hydrogenation is carried out under a pressure 10-15 atm in a polythermal regime (temperature gradually rises to 120° C. at the expense of heat released in the reaction).

After hydrogen consumption is finished and the reaction mass has remained for an hour under the same conditions (stiffing; hydrogen pressure, 10-15 atm; temperature, 100-120° C.), hydrogen is pushed out of the reactor with nitrogen, and the catalysate is extruded through a Druck-filter into a heated (90-100° C.) crystallizing tank, which is then supplemented with 20 ml of the seed water solution (a solution of synthetic succinic acid with certified biological activity obtained as described in Example 4). The concentration of seed in the entire mass is 0.001%. The process of crystallization is carried out in a regime of variable-rate temperature decreasing. The rate of cooling is regulated in such a way that approximately a half of succinic acid would get sedimented after 13-17 min. Then the rate of cooling is lowered to a level that would provide sedimentation of ~70% of total succinic acid within 35-40 min since the beginning of cooling. The cooling is proceeded until temperature reaches 8-10° C. (the entire crystallization process takes 1.5-2 h), and the sediment is separated from the source solution on a Nutsche-filter, the solution returning into the cycle. The source solution is used both to prepare the initial solution of succinic anhydride and to modify the "fresh" catalyst. The acid is dried in a rack-dryer at a temperature 90-95° C. The resulted succinic acid (yield, ~80%) is of high quality: assay, 100%; melting point, 187-187.5° C.; no unsaturated acids. With the source solution recycled three times, the yield of succinic acid reaches 99.7% of theoretically expected.

EXAMPLE 6

The procedure of modification is conducted in a hydrogenation reactor (V=630 dm$^3$) with a mixer (2500 rpm). The apparatus is loaded with 240 ml of water, 210 g of succinic acid, 210 g of maleic acid and 4200 g (dry weight equivalent) of PF catalyst, whose active phase, according to the specification, is polychlorohydroxo-complexes of palladium promoted with iron salts. The air is forced out of the reactor with nitrogen, which is then replaced with hydrogen. After sealing the reactor, its contents are heated to 30° C., and modification of catalyst is carried out for 1.5 hours under continuous stiffing.

After modification is finished, the reactor is fed, under nitrogen pressure, a maleic anhydride (maleic acid) solution (120 kg/120 liters of water) heated to 50° C. The nitrogen-hydrogen mixture is pushed out of the reactor with hydrogen and, after a pressure of 20 atm is reached, mixing and heating are turned on. Hydrogenation is carried out at 50-110° C. under a pressure 15-20 atm for 40 min After incubation for 0.5 hours and purging the reactor with nitrogen, its contents are filtered through a heated Druck-filter for separation of the catalyst. The crystallizing tank is supplemented with succinic acid (as water solution) obtained according to Example 4 and used as a seed. The concentration of seed in the entire mass is 0.01%.

The crystallization is carried out during controlled cooling (see Example 5).

The resulting product is succinic acid with assay 99.92% (without unsaturated compounds). The yield after 3 cycles of source solution recycling is 99.2% of theoretically expected.

EXAMPLE 7

In order to hydrogenate maleic anhydride, the catalyst "palladium on Sibunite" is used, which is obtained by applying palladium hydroxo-complexes on pyrocarbon. The catalyst is modified with maleic and fumaric acids (5:1). The modification is conducted in an apparatus with a jacket and mixer (V=0.75 dm$^3$), which is loaded with 300 ml of water, 0.05 g of acid mixture and 5.1 g of catalyst. The apparatus is purged with nitrogen-argon mixture (10:1, v/v). The reactor jacket is filled with cooled water (5° C.), the modification is carried out under continuous stirring for 2 hours.

An autoclave (V=1 dm$^3$) is loaded with 300 ml of water and 205 g of maleic anhydride, this followed by blowing through the autoclave with nitrogen and heating its contents to 30-40° C. under stirring—until all is dissolved. Then the apparatus is fed, under nitrogen pressure, the suspension of modified catalyst, and hydrogenation is carried out at 90° C. under the pressure of 10 atm.

After separation of the catalyst by "hot" filtration, the solution of succinic acid is transferred into a crystallizing tank supplied with the water solution of seed, a mixture of succinic acid prepared according to Example 6 and "natural" succinic acid (1:1). The concentration of seed in the entire mass is 0.008 wt. %. The crystallization is carried out during stepwise cooling (see Example 5).

The product obtained is succinic acid of excellent quality (assay, 100%; melting point 187.9-188° C.), with the yield 98.8% of theoretically expected (after 3 cycles of source solution recycling).

EXAMPLE 8

Modification of Escat-16 catalyst (0.5% palladium in reduced form on coco-tree carbon) is conducted right in the hydrogenation reactor (V=1 dm$^3$). 7.5 g of ground catalyst (size of main-fraction particles, 63-100 µm) is placed into an autoclave, which is then loaded with 650 ml of 0.06 wt. % solution of succinic acid. The reactor is purged with nitrogen and filled with a nitrogen-hydrogen mixture (1:1, v/v). After turning on stirring, temperature is raised to 40° C., and the catalyst suspension remains under these conditions for an hour.

After modification is finished, the nitrogen-hydrogen mixture is replaced with nitrogen, the suspension is supplied with 250 g of maleic acid, and the apparatus is sealed and filled with hydrogen. Then hydrogenation is started and carried out under a hydrogen pressure 15 atm and temperature 100° C.

After hydrogen consumption is finished, the catalysate remains for an hour under the conditions of hydrogenation and then, with hydrogen replaced with nitrogen and catalisate separated on a heated filter, the solution obtained is directed into a crystallization tank heated to 90° C.

The crystallization of succinic acid is carried out as described in Example 5. The seed used is succinic acid obtained by pyrolysis of amber crumb. The concentration of seed in the entire mass is 0.001%.

The conditions described allow to obtain succinic acid with assay not less than 99.9% of theoretically expected and without impurities. The yield of succinic acid is 80.2, 90.8 and 99.1% of theoretically expected (after 1, 2 and 3 cycles respectively).

EXAMPLE 9

The experiment is conducted as described in Example 7 with the difference being that the catalyst used is palladium (in the oxidized form) on silica gel (ASM; granulated; granule size, 60-100 µm). 9.2 g of catalyst are stirred in 300 ml of 0.03 wt. % water solution of succinic acid at 25° C. under a nitrogen/hydrogen (5:1, v/v) atmosphere for 1.5 hours.

All the subsequent procedures are performed as described in Example 7, the concentration of seed used in the process of crystallization being 0.001% (in the entire mass). Succinic acid used as the seed is synthetic with certified biological activity.

The yield of succinic acid grows from $1^{st}$ to $3^{rd}$ cycle, reaching 98.9% of theoretically expected. The quality of acid remains high (no unsaturated acids assay, not less than 99.9 wt. %).

EXAMPLE 10

The apparatus described in Example 4 is used, the catalyst modified is nickel-palladium on fibrous asbestos (palladium in the hydroxide form promoted with a nickel salt).

The conditions of modification: 100 ml of water; 1.035 g of catalyst; 1 g of fumaric acid; stirring at 70° C. under helium-hydrogen atmosphere (1:5, v/v).

The modified catalyst is pressed into a reactor previously purged with helium and fed a suspension of 207.1 g of fumaric acid in 600 ml of water heated to 80° C. The reactor is filled with hydrogen, and hydrogenation is carried out at 120° C. under a pressure 25 atm.

The conditions of crystallization are the same as in Example 4. In the product obtained, there are no maleic or fumaric acid, assay 99.7 wt. %. The yield of succinic acid is 99.1% of theoretically expected (after 3 cycles of source solution recycling).

Additional information for Examples 4-10 is given in Table 1.

TABLE 1

Modification of palladium catalysts and hydrogenation of maleic anhydride, maleic and fumaric acids

| Ex. no | Catalyst | Active phase | Active phase content, wt. % | support | Initial hydrogenated compound | Modifier | Conc. (wt. %) of acid in the solution | Conc. (wt. %) of catalyst in the acid solution | Pd/acid (total acids) | Modification conditions (medium, temperature, time) |
|---|---|---|---|---|---|---|---|---|---|---|
| 4 | NPF-1 | Pd-PCHC[1] (Ni salt) | 0.2 0.2 | carbon | maleic acid | MA | 0.5 | 4.6 | 1:50 | Ar 20° 1 h |
| 5 | POUB-0.8 | Pd in reduced form | 0.8 | carbon | maleic anhydride | SA | 0.012 | 1.5 | 1:1 | $N_2/H_2$ = 1:1 (v) 40-50° 30-40 min |
| 6 | PF | Pd-PCHC[1] (Fe salt) | 0.1 0.1 | carbon | maleic anhydride | SA/MA = 1:1 | 0.0175 | 1.75 | 1:100 | $H_2$ 30° 1.5 h |
| 7 | "Kalan" catalyst | Pd-HC[2] | 0.5 | Sibunite[3] | maleic anhydride | FA/MA = 1:5 | 0.016 | 1.7 | 1:2 | $N_2/H_2$ = 10:1 (v) 5° 2 h |
| 8 | Escat-16, ground | Pd in reduced form | 0.5 | $Al_2O_3$ | maleic acid | SA | 0.058 | 1.15 | 1:10 | $N_2/H_2$ = 1:5 (v) 40° 1 h |
| 9 | — | Pd | 1.0 | $SiO_2$ | maleic anhydride | SA | 0.037 | 3.07 | 1:1 | $N_2/H_2$ = 5:1 (v) 25° 1.5 h |
| 10 | — | Pd (Ni salt) | 1.0 3.0 | fibrous asbestos | fumaric acid | FA | 0.7 | 1.03 | 1:100 | $He/H_2$ = 1:5 (v) 70° 2 h |

| | Hydrogenation | | | | Crystallization | |
|---|---|---|---|---|---|---|
| Ex. no | Temp., ° C. | Pressure, atm | Catalyst content, % of initial compound | Yield, % of theoretically expected | seed | Conc. of seed in the entire mass (%) |
| 4 | 90-100 | 20 | 2.0 | I cycle 81.2 II cycle 92.3 III cycle 99.5 | a[4] | 0.01 |
| 5 | 40-120 | 10-15 | 1.5 | I cycle 80.0 II cycle 90.5 III cycle 99.7 | b[5] | 0.001 |
| 6 | 50-110 | 15-20 | 3.5 | I cycle 80.9 II cycle 91.5 III cycle 99.2 | b | 0.01 |
| 7 | 90 | 10 | 2.5 | I cycle 79.5 II cycle 91.5 III cycle 98.8 | a + b 1:1 | 0.008 |
| 8 | 80 | 20 | 3.0 | I cycle 80.2 II cycle 90.8 III cycle 99.1 | a | 0.008 |

TABLE 1-continued

Modification of palladium catalysts and hydrogenation of maleic anhydride, maleic and fumaric acids

| 9 | 100 | 15 | 4.5 | I cycle 79.3<br>II cycle 90.7<br>III cycle 98.9 | b | 0.001 |
| 10 | 120 | 25 | 0.5 | I cycle 80.7<br>II cycle 90.6<br>III cycle 99.1 | a | 0.01 |

SA, succinic acid;
MA, maleic acid;
FA, fumaric acid
[1]PCHC, polychlorohydroxo-complexes
[2]HC, hydroxo-complexes
[3]pyrocarbon support
[4]a, "natural" SA, obtained by pyrolysis of amber
[5]b, synthetic SA with certified biological activity

EXAMPLE 11

Test for Acute Toxicity of Product Samples

The test was performed on white rat females (220-250 g), which were administered for 14 days with succinic acid. Once per day, 2.2-2.5 ml of 5% succinic acid (5000 mg/kg body wt.) were injected perorally, using a stomach pump. For each Example, a group of 10 animals was used. The results are given at Table 2.

TABLE 2

Test for acute toxicity of samples

| Example no. | 11 day | 12 day | 13 day | 14 day | Total died |
|---|---|---|---|---|---|
| 1 | — | — | — | — | 0 |
| 2 | — | — | — | — | 0 |
| 3 | — | — | — | 2 | 2 |
| 4 | — | 1 | 1 | 1 | 3 |
| 5 | — | — | 2 | 1 | 3 |
| 6 | 1 | — | — | 2 | 3 |
| 7 | — | — | 2 | 2 | 4 |
| 8 | — | 1 | 1 | 1 | 3 |
| 9 | — | — | 2 | 1 | 3 |
| 10 | — | — | 1 | 2 | 3 |
| Natural acid | — | — | 1 | 2 | 3 |

As seen from Table 2, the first two samples have no lethal effect and can be considered low-hazard compounds. The $3^{rd}$ sample is more toxic. To put an additional control, we have performed an extra test for products of Examples 1 and 2, with the dose of succinic acid doubled (a 10% solution of succinic acid was used, which corresponds to 10000 mg/kg body wt.). Not a single animal died. This experiment also shows that the toxicological properties of SA obtained by Examples 4-10 are identical to those of "natural" SA.

EXAMPLE 12

Test for Genotoxicity of Product Samples and Determination of their Radioprotective Properties The test for genotoxicity was performed on young laboratory mice males (18-20 g; 6 animals in each group). The experiment was carried out in two stages. First, succinic acid samples were tested for mutagenic properties. The control animals were given water. In the experimental groups, animals were given a standard feed supplemented either with succinic acid obtained by Examples 1-10 or with "natural" Sa (20 mg/kg body wt.) In the next stage, radioprotective properties of samples were examined. The animals were irradiated with gamma rays (1.3 Gy) and then were fed, for 48 h, a meal containing succinic acid (20 mg/kg body wt.; either obtained by Examples 1-10 or "natural"). Used as a positive control was one of the animal groups taken 48 h after irradiation. This control group did not receive succinic acid.

Genotoxicity was estimated by the micronucleus test (by the presence of micronucleus, i.e., an optically dense formation, in the cell) using a smear of erythroid cells isolated from the bone marrow of the animal's hind limb. For each animal, 2000 cells were analyzed, with the polychromic/normochromic erythrocyte ratio determined after counting 200 cells.

The results are given in Table 3.

TABLE 3

Genotoxicity of succinic acid samples

| Sample | Number of micronuclei per 2000 cells |
|---|---|
| Control | 5.0 ± 1.0 |
| Example 1 | 5.5 ± 0.8 |
| Example 2 | 5.5 ± 1.0 |
| Example 3 | 5.0 ± 0.6 |
| Example 4 | 5.5 ± 1.0 |
| Example 5 | 5.0 ± 1.0 |
| Example 6 | 4.5 ± 1.0 |
| Example 7 | 5.0 ± 1.0 |
| Example 8 | 5.0 ± 0.8 |
| Example 9 | 5.0 ± 1.0 |
| Example 10 | 5.0 ± 1.0 |
| "Natural acid" | 5.0 ± 1.0 |

The mutation norm is 5.0±1.0 micronuclei per 2000 cells. As seen from Table 3, all the samples are not genotoxic.

TABLE 4

Radioprotective properties of succinic acid samples

| Sample | Number of micronuclei per 2000 cells |
|---|---|
| Positive control | 23.0 ± 1.2 |
| Example 1 | 25.5 ± 1.0 |
| Example 2 | 22.5 ± 1.0 |
| Example 3 | 16.0 ± 1.6 |
| Example 4 | 12.5 ± 2.0 |
| Example 5 | 12.0 ± 1.2 |
| Example 6 | 12.5 ± 1.0 |
| Example 7 | 11.5 ± 1.8 |
| Example 8 | 12.0 ± 1.5 |
| Example 9 | 11.0 ± 1.6 |

TABLE 4-continued

Radioprotective properties of succinic acid samples

| Sample | Number of micronuclei per 2000 cells |
|---|---|
| Example 10 | 12.5 ± 1.0 |
| "Natural acid" | 12.0 ± 1.6 |

The number of mutations 16±2 is a critical value for the development of irreversible consequences of irradiation. As seen from Table 4, the samples obtained by Examples 1 and 2 have no evident radioprotective effect, the sample by Example 3 is "close to the dividing line", whereas the samples by Examples 4-10 and the sample of "natural" SA "lead out animals into the safe zone", i.e., they are evident radioprotectors, helping the animals to survive without therapy.

EXAMPLE 13

Test for Adaptogenic Properties (Test for Biological Activity)

The test analyses the effect of 6-hour immobilization stress on Wistar rat males (200-250 g). The animals were fixed while lying flat on their back, with their legs secured. The development of acute stress was confirmed by a characteristic change in the leukogram of peripheral blood. Blood was taken from the caudal vein: 10 µl for counting blood corpuscles and 20 µl for preparing a smear with its subsequent staining by Romanovsky-Giemsa). The number of leukocytes (per ml of blood) increased from 5600±600 to 8800±800 ($n=8$, $p <0.02$), with the percentage of segmented cells increasing from 24±4% to 37±5%, the percentage of lymphocytes, on the contrary, decreasing from 75±7% to 61±6%, and with eosinophils completely disappearing from the bloodstream. In animals of the stress group probed 6 h after immobilization, a full-scale stress triad was found:

- all animals revealed numerous hemorrhages in the mucosa of stomach and small intestine;
- thymus weight decreased from 400±50 mg (in control animals) to 100±50 mg (in the stress-subjected animals);
- adrenal weight increased from 16±3 mg to 25±4 mg.

Using this model of acute stress, we tested samples of succinic acid obtained by Examples 1-10 and a sample of "natural" acid, measuring the characteristic changes in the peripheral blood leukogram. 12 groups of animals were tested, with 9 Wistar rat males (200-250 g) in each group. First group: 10 min prior immobilization, the animals were injected (perorally, with the help of a stomach pump) with 1.5 ml of 1% starch solution. Second twelve groups: 10 min prior immobilization, the animals were injected (perorally, with the help of a stomach pump) with 1.5 ml of 1% succinic acid obtained by Examples 1-10 or "natural". Blood was taken from the caudal vein at the moment of immobilization and 6 hours later, and stained blood smears were prepared to calculate the leukogram. The result are given in Table 5.

TABLE 5

Data on the peripheral blood leukogram

| Group no. 1 | Number of leukocytes in 1 µl of blood | | Segmented cells, % | | Lymphocytes, % | | Eosinophils, % | |
|---|---|---|---|---|---|---|---|---|
| | before 2 | 6 h after 3 | before 4 | 6 h after 5 | before 6 | 6 h after 7 | before 8 | 6 h after 9 |
| Control | 6100 ± 570 | 9100 ± 910 | 21 ± 3 | 34 ± 4 | 77 ± 5 | 65 ± 6 | 2 ± 1 | 0 |
| Group 1 (placebo control) | 5700 ± 460 | 8700 ± 660 | 22 ± 3 | 33 ± 4 | 76 ± 7 | 65 ± 7 | 2 ± 2 | 0 |
| Group 2 (by Ex. 1) | 5900 ± 820 | 7900 ± 450 | 21 ± 2 | 29 ± 3 | 78 ± 4 | 69 ± 5 | 2 ± 4 | 0 |
| Group 3 (by Ex. 2) | 5700 ± 460 | 7700 ± 870 | 21 ± 4 | 30 ± 3 | 76 ± 4 | 70 ± 5 | 2 ± 2 | 0 |
| Group 4 (by Ex. 3) | 5700 ± 780 | 7100 ± 450 | 22 ± 3 | 26 ± 3 | 76 ± 6 | 73 ± 5 | 2 ± 6 | 0.5 ± 4 |
| Group 5 (by Ex. 4) | 5900 ± 821 | 7100 ± 650 | 21 ± 2 | 24 ± 3 | 77 ± 4 | 74 ± 8 | 2 ± 4 | 1.5 ± 6 |
| Group 6 (by Ex. 5) | 6000 ± 460 | 7200 ± 500 | 22 ± 4 | 24 ± 3 | 76 ± 5 | 75 ± 4 | 2 ± 6 | 1.5 ± 8 |
| Group 7 (by Ex. 6) | 5800 ± 470 | 7000 ± 660 | 21 ± 3 | 25 ± 3 | 77 ± 5 | 74 ± 6 | 2 ± 2 | 1.0 ± 2 |
| Group 8 (by Ex. 7) | 6000 ± 500 | 7200 ± 570 | 23 ± 3 | 26 ± 3 | 75 ± 7 | 73 ± 6 | 2 ± 1 | 1.5 ± 4 |
| Group 9 (by Ex. 8) | 5900 ± 430 | 7000 ± 580 | 21 ± 4 | 24 ± 2 | 77 ± 5 | 75 ± 4 | 2 ± 6 | 1.5 ± 3 |
| Group 10 (by Ex. 9) | 5800 ± 360 | 7000 ± 540 | 22 ± 3 | 25 ± 6 | 76 ± 6 | 74 ± 6 | 2 ± 4 | 1.5 ± 2 |
| Group 11 (by Ex. 10) | 5800 ± 810 | 7000 ± 450 | 22 ± 3 | 24 ± 4 | 76 ± 5 | 74 ± 4 | 2 ± 2 | 1.5 ± 2 |
| Group 12 ("natural" SA) | 5900 ± 600 | 7100 ± 480 | 23 ± 2 | 25 ± 3 | 75 ± 4 | 74 ± 4 | 2 ± 4 | 1.5 ± 3 |

As seen from Table 5, the succinic acid samples by Examples 1 and 2 possess slight adaptogenic properties, the sample by Example 3 is at the "borderline", while the samples by Examples 4-10 and the sample of "natural" acid are evident adaptogens, almost completely compensating for the consequences of immobilization stress. It is this test that turned out to be the most informative, inexpensive and reproducible when used to control quality of the technological process. The acid obtained is relatively good if the percentage of eosinophils is not less than 0.5% (25% of the initial level). In practice, the batches of SA used as the "seed" of the crystallization process guarantee the percentage of eosinophils to remain at a level of 1.0% (50% of the initial level) or more. The same method is used to presort the product samples and batches of SA. Every new party of animals (of a new line or obtained from another nursery) is subjected to the control test for immobilization stress. The animals are tested for the stress leukogram of peripheral blood and for development of the classical stress triad: leukocytosis with lymphopenia, thymus regression and adrenal hypertrophy. The results of this testing define the background parameters.

EXAMPLE 14

Test for Cardiotonic Properties of Product Samples

The differences in the biological activity of various succinic acid batches were first revealed in the process of therapy of cardiologic patients. With the synthetic SA substituting for "natural" one, the patients started to notice a substantial (or even complete) fall in the effectiveness of SA—but not in all batches of the preparation. Demonstration of this effect made it necessary to elaborate such a technology of SA synthesis, which would guarantee its high biological activity.

The test for cardiotonic activity of product samples was performed by measuring the dynamics of alteration of the functional class of cardiac failure. The functional class can be determined quite accurately by analyzing the everyday life activities according to a specific activity scale. The authors of this technique suppose that the criteria developed by NYHA (New York Heart Association) cannot provide accurate determination of functional class, since widely used terms, such as "everyday physical activity", "sub-everyday activity" are not specific. On the basis of multiple tests, in which patients exercised on a treadmill, the authors calculated a scale of metabolic expenses for each kind of life activity (see Goldman L., Hashimoto B., Cook F. et al., Comparative reproducibility and validity of systems for assessing cardiovascular functional class: advantages of a new specific activity scale (1981) Circulation 64 (6):1227-34). This inquiry is designed to be used by medical personnel, interviewing a patient. After calculating the sum of possible energy expenses, the functional class of the patient is determined according to the summary criteria of the specific activity scale (Table 6).

TABLE 6

Summary criteria of the specific activity scale

CLASS I. Patients with chronic circulatory insufficiency, whose physical activity is equal to or more than 7 MET.
CLASS II. Patients with chronic circulatory insufficiency, whose physical activity is not more than 5 MET.
CLASS III. Patients with chronic circulatory insufficiency, whose physical activity is not more than 2 MET.
CLASS IV. Patients with chronic circulatory insufficiency, who cannot reach the physical activity level of 2 MET.

In the tests, the patient groups were formed so that the people of the same functional class were equally distributed among different groups. Severe patients (of IV functional class; those having oncological diseases or suffered myocardial infarction/stroke to the brain 60 days or less before) were not admitted to the tests. The distribution of patients among groups was governed by a random number generator. The tests were carried out by the following protocol. Each patient took 100 mg of the preparation twice per day (in the morning and after lunch) during 3 months—against the background of a standard therapy administered by a physician. One group was given a placebo (glucose); others were treated with the succinic acid preparations by Examples 1-10 and with "natural" succinic acid. All the samples and placebo were encoded before sending into the clinic, so none of those involved into the tests (patients, physicians, medical personnel and the manager of tests) was aware of the nature of samples.

The functional class of patients was determined several times: at the beginning of tests (before the formation of test groups) and after 30, 60 and 90 days of treatment with the test samples. The estimation was performed on the basis of the activity scale (Table 7).

TABLE 7

| Questions | Yes | No |
|---|---|---|
| 1. Can you go down one flight of stairs without stop? (4.5-5.2 MET)* | go to Question 2 | go to Question 4 |
| 2. Can you carry something 8 steps upstairs without stop? (5.0-5.5 MET) or | go to Question 3 | III FC |
|    a) Can you finish coitus without stop? (5.0-5.5 MET) or | | |
|    b) Can you work in a garden, loosen soil? (5.6 MET) or | | |
|    c) Can you skate, dance (5.0-5.6 MET) or | | |
|    d) Can you walk along an even road at 5 km/h? (5.6-6.0 MET) | | |
| 3. Can you carry a 10-kg load 8 steps upstairs? (10.0 MET) or | I FC | II FC |
|    a) Can you lift a 30-kg load? (8.0 MET) or | | |
|    b) Can you shovel snow or mud? (7.0 MET) or | | |
|    c) Can you ski, play basketball, football etc.? (7.0-10.0 MET) or | | |
|    d) Can you walk or run at 8 km/h? (9.0 MET) | | |
| 4. Can you take a shower without break and rest? (3.6-4.2 MET) or | III FC | go to Question 5 |
|    a) Can you get undressed and make the bed without help? (3.9-5.0 MET) or | | |
|    b) Can you mop a floor (4.2 MET) or | | |
|    c) Can you hang washing on a line? (4.4 MET) or | | |
|    d) Can you clean up a window? (3.7 MET) | | |
|    e) Can you walk at 4 km/h? (3.0-3.5 MET) or | | |
|    f) Can you play bowls? (3.0-4.4 MET) or | | |
|    g) Can you play golf? (4.5 MET) or | | |
|    h) Can you work with a lawn-mower? (4.0 MET) | | |
| 5. Can you get dressed after sleep without need to stop because of circulation insufficiency symptoms? | III FC | IV FC |

*MET are metabolic units

The dynamics of decoded functional class changes is given in Table 8.

TABLE 8

The functional class of cardiac insufficiency in patients under observation (evaluated with the activity scale)

| | Functional class of cardiac insufficiency | | | | | | | | | | | | | | | |
|---|---|---|---|---|---|---|---|---|---|---|---|---|---|---|---|---|
| | I | | | | II | | | | III | | | | IV | | | |
| Group | 0 | 30 | 60 | 90 | 0 | 30 | 60 | 90 | 0 | 30 | 60 | 90 | 0 | 30 | 60 | 90 |
| 1 | 2 | 3 | 4 | 5 | 6 | 7 | 8 | 9 | 10 | 11 | 12 | 13 | 14 | 15 | 16 | 17 |
| Placebo | 8 | 8 | 8 | 9 | 7 | 7 | 7 | 6 | 5 | 5 | 5 | 5 | 0 | 0 | 0 | 0 |
| By Example 1 | 8 | 8 | 9 | 9 | 7 | 7 | 6 | 7 | 5 | 5 | 5 | 4 | 0 | 0 | 0 | 0 |
| By Example 2 | 8 | 8 | 8 | 8 | 7 | 7 | 8 | 8 | 5 | 5 | 4 | 4 | 0 | 0 | 0 | 0 |
| By Example 3 | 8 | 9 | 9 | 10 | 7 | 7 | 7 | 7 | 5 | 4 | 4 | 3 | 0 | 0 | 0 | 0 |
| By Example 4 | 8 | 8 | 9 | 13 | 7 | 7 | 9 | 6 | 5 | 5 | 3 | 1 | 0 | 0 | 0 | 0 |
| By Example 5 | 8 | 8 | 9 | 14 | 7 | 7 | 7 | 5 | 5 | 5 | 4 | 1 | 0 | 0 | 0 | 0 |
| By Example 6 | 8 | 10 | 11 | 14 | 7 | 6 | 6 | 5 | 5 | 4 | 3 | 1 | 0 | 0 | 0 | 0 |
| By Example 7 | 8 | 9 | 13 | 15 | 7 | 6 | 5 | 4 | 5 | 5 | 2 | 1 | 0 | 0 | 0 | 0 |
| By Example 8 | 8 | 10 | 11 | 14 | 7 | 6 | 6 | 5 | 5 | 4 | 3 | 1 | 0 | 0 | 0 | 0 |
| By Example 9 | 8 | 10 | 11 | 14 | 7 | 6 | 6 | 5 | 5 | 4 | 3 | 1 | 0 | 0 | 0 | 0 |
| By Example 10 | 8 | 10 | 10 | 14 | 7 | 5 | 7 | 5 | 5 | 4 | 3 | 1 | 0 | 0 | 0 | 0 |
| "Natural" SA | 8 | 10 | 9 | 14 | 7 | 6 | 8 | 5 | 4 | 4 | 3 | 1 | 0 | 0 | 0 | 0 |

As seen from Table 8, the groups that were given preparations by Examples 1 and 2 show a slight positive dynamics; the dynamics is more expressed in the group treated with the preparation by Example 3; however, it is much less pronounced than that in the groups treated with preparations by Examples 4-10 and with "natural" acid, which demonstrate high cardiotonic properties.

The biological tests of preparations by Examples 11-14 revealed that the SA samples obtained by Examples 1 and 2 do not possess high biological activity. The sample by Example 3 has a higher activity but it is far from that of "natural" SA. The samples by Example 4-10 completely correspond to "natural" acid. At the same time, the use of biologically active acid as the "seed" is shown to guarantee a stable yield of succinic acid with high biological activity and with evident adaptogenic properties.

What is claimed is:

1. A method for preparing succinic acid, comprising:
    producing a modified palladium-containing catalyst by using an acid and liquid-phase hydrogenation of unsaturated acid compounds on the modified catalyst at a temperature of between 40 and 120 degrees C. and a pressure of 10-25 atm;
    separating the catalyst from the succinic acid;
    wherein the modification of the catalyst is performed on a substrate having the palladium-containing catalyst delivered thereon, the delivery being performed in an oxygen-free atmosphere;
    the delivery being performed in an aqueous medium of succinic, maleic or fumaric acids and/or their mixtures at a $Pd^{2+}$/acid ratio of 1:1-1:100;
    hydrogenating the liquid-phase unsaturated acid compounds selected from maleic, fumaric acids or their anhydrides or their mixtures; and
    crystallizing the succinic acid from an aqueous solution containing 0.001-0.01 wt. % succinic acid seed.

2. The method of claim 1, wherein the oxygen-free atmosphere includes any of nitrogen, hydrogen, argon, helium and/or their mixture, and the process of modification occurs in a temperature range of 5 to 70 degrees Centigrade, and with a concentration of the catalyst aqueous solution in a range of 0.1 to 1.5 wt. %.

3. The method of claim 2, wherein the process of modification is carried out at a temperature chosen from the range of 15 to 40 degrees Centigrade at the catalyst aqueous solution concentration within the range of 0.1 to 1.0 wt. % and a concentration of the modifying acid compound solution within the range of 0.01 to 0.7%.

4. The method of claim 1, wherein the crystallization seed is a succinic acid of natural origin.

5. The method of claim 1, wherein the crystallization seed is a synthetic succinic acid.

6. The method of claim 1, wherein the crystallization seed is both a succinic acid of natural origin and a synthetic succinic acid.

* * * * *

UNITED STATES PATENT AND TRADEMARK OFFICE
CERTIFICATE OF CORRECTION

PATENT NO. : 8,546,611 B2
APPLICATION NO. : 13/061147
DATED : October 1, 2013
INVENTOR(S) : Roman Anatolievich Trunin et al.

It is certified that error appears in the above-identified patent and that said Letters Patent is hereby corrected as shown below:

On the Title Page

Item (76), should read as follows:
(76) Inventors: Roman Anatolievich Trunin, Moscow (RU); Mikhail Lvovich Uchitel, Mytishi (RU); Evgenij Iljich Maevskij, Pushino (RU); Vladimir Izrailevich Heifets, Tula (RU); Donna Kasseinova, Palos Verdes Estates, CA (US); Larisa Petrovna Pivonenkova, Tula (RU); Tatiana Borisovna Lubimova, Tula (RU)

Signed and Sealed this
First Day of January, 2019

Andrei Iancu
*Director of the United States Patent and Trademark Office*